(12) United States Patent
Yu et al.

(10) Patent No.: US 10,352,830 B2
(45) Date of Patent: Jul. 16, 2019

(54) DEVICES AND METHODS FOR INSPECTING A WHEEL

(71) Applicant: GENERAL ELECTRIC COMPANY, Schenectady, NY (US)

(72) Inventors: Xun Yu, Shanghai (CN); Ran Li, Shanghai (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 211 days.

(21) Appl. No.: 15/102,424

(22) PCT Filed: Dec. 12, 2014

(86) PCT No.: PCT/US2014/069982
§ 371 (c)(1),
(2) Date: Jun. 7, 2016

(87) PCT Pub. No.: WO2015/089381
PCT Pub. Date: Jun. 18, 2015

(65) Prior Publication Data
US 2017/0010186 A1    Jan. 12, 2017

(30) Foreign Application Priority Data

Dec. 13, 2013 (CN) .......................... 2013 1 0683975

(51) Int. Cl.
*G01M 17/10* (2006.01)
*B61K 9/12* (2006.01)
(Continued)

(52) U.S. Cl.
CPC .............. *G01M 17/10* (2013.01); *B61K 9/12* (2013.01); *G01N 29/041* (2013.01); *G01N 29/24* (2013.01);
(Continued)

(58) Field of Classification Search
CPC ....... G01M 17/10; B61K 9/12; G01N 29/041; G01N 29/24; G01N 2291/0289
(Continued)

(56) References Cited

U.S. PATENT DOCUMENTS 3,951,563 A * 4/1976 Ravenhall .............. G01B 7/315
29/894.325
2006/0055399 A1 * 3/2006 Georgeson ......... G01N 29/2481
324/232
(Continued)

FOREIGN PATENT DOCUMENTS

CN      101143591 A      3/2008
CN      101149358 A      3/2008
(Continued)

OTHER PUBLICATIONS

International Search Report and Written Opinion issued in connection with corresponding PCT Application No. PCT/US2014/069982 dated Apr. 9, 2015.
(Continued)

*Primary Examiner* — Tarun Sinha
(74) *Attorney, Agent, or Firm* — Mintz Levin Cohn Ferris Glovsky and Popeo, P.C.

(57) ABSTRACT

The present invention discloses a inspection device for detecting a defect of a metal object, where the inspection device includes a main base, at least one main magnetic module, and a main inspection module. The at least one main magnetic module is installed on the main base, for attaching the main base onto the metal object under an action of a magnetic force. The main inspection module is installed on the main base, to detect at least one type of defect of the metal object. The present invention further discloses a wheel defect inspection method and a wheel defect inspection device. The metal object defect inspection device may
(Continued)

implement automatic detection of a defect on a whole circumference of a wheel.

16 Claims, 15 Drawing Sheets

(51) Int. Cl.
    *G01N 29/04*     (2006.01)
    *G01N 29/24*     (2006.01)

(52) U.S. Cl.
    CPC ............ *G01N 2291/0289* (2013.01); *G01N 2291/106* (2013.01); *G01N 2291/2696* (2013.01)

(58) Field of Classification Search
    USPC .......................................... 73/639
    See application file for complete search history.

(56) References Cited

U.S. PATENT DOCUMENTS

| | | | | |
|---|---|---|---|---|
| 2007/0137302 A1* | 6/2007 | Fetzer | ............ | G01N 29/225 73/649 |
| 2010/0275691 A1* | 11/2010 | Roberts | ............ | G01N 27/90 73/622 |
| 2012/0060609 A1 | 3/2012 | Fukutomi et al. | | |
| 2012/0325005 A1 | 12/2012 | Oliver et al. | | |

FOREIGN PATENT DOCUMENTS

| | | | | |
|---|---|---|---|---|
| CN | 101256173 A | 9/2008 | | |
| CN | 101639463 A | 2/2010 | | |
| CN | 101666781 A | 3/2010 | | |
| CN | 201434859 Y | 3/2010 | | |
| CN | 201464429 U | 5/2010 | | |
| CN | 101788533 A | 7/2010 | | |
| CN | 201535767 U | 7/2010 | | |
| CN | 102841147 A | 12/2012 | | |
| DE | 19925394 A1 | 12/2000 | | |
| DE | 10257709 C1 | 12/2003 | | |
| DE | 10336042 A1 | 3/2005 | | |
| DE | 19943744 B4 | 1/2006 | | |
| DE | 202006019808 | * | 4/2007 | ............ G01M 17/10 |
| DE | 202006019808 U1 | 4/2007 | | |
| EP | 0889322 A2 | 1/1999 | | |
| JP | 2012173068 A | 9/2012 | | |
| KR | 20100076642 A | 7/2010 | | |
| WO | 9013814 A1 | 11/1990 | | |

OTHER PUBLICATIONS

Rockstroh et al., "Ultrasonic and Eddy-Current Inspection of Rail Wheels and Wheel Set Axles", 17th World Conference on Nondestructive Testing, Shanghai, China, pp. 1-10, Oct. 25-28, 2008.

Unofficial English Translation of Chinese Office Action issued in connection with corresponding CN Application No. 201310683975.4 dated Dec. 29, 2016.

* cited by examiner

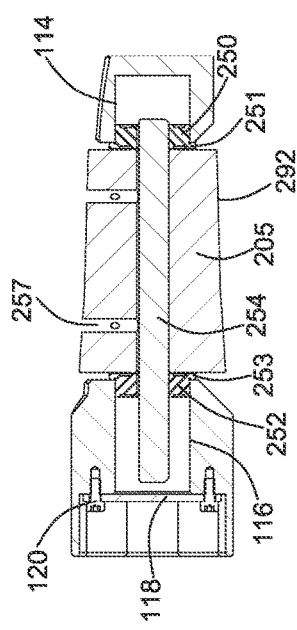
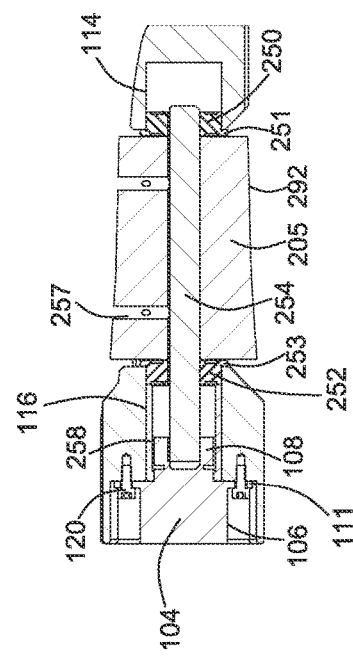

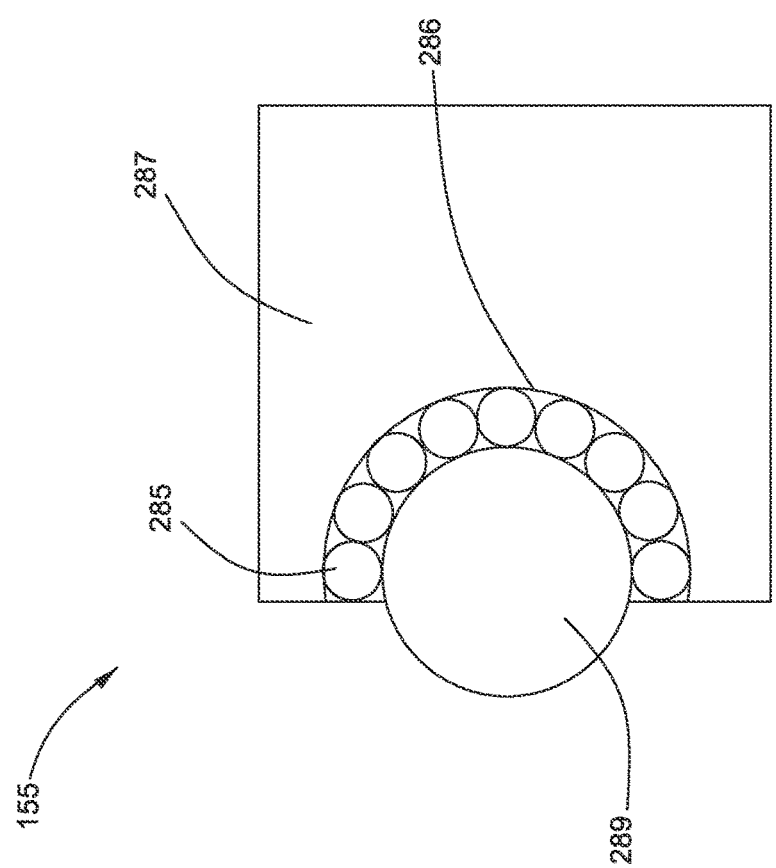

DEVICES AND METHODS FOR INSPECTING A WHEEL

TECHNICAL FIELD

Embodiments described herein relate to a metal object defect inspection device, and in particular, to a wheel defect inspection device.

BACKGROUND

Railway transportation plays a big part in urban transportation. In order to ensure safe running of the railway transportation, a higher requirement is put forward for quality of wheels. In order to prevent a defective wheel from causing an accident during running, and ensure driving safety of a train, it is required to perform defect detection for a tread, a wheel rim, a spoke, and other parts of the wheel. Meanwhile, it is hoped to perform on-line detection (defect detection) without disassembling a wheel set.

Major causes of a wheel defect include: during smelting and processing of steel used for the wheel, some defects such as gas holes, blisters, inclusions, and scratches are often generated on a surface of the wheel or inside the wheel. Because of existence of these defects, stress concentration may be caused during running of the wheel. In an area of stress concentration, a bearing capacity of metal is small, cracks are prone to extend; under a situation of continuous bearing, the cracks continuously expands, and exfoliation and chipping are generated on the surface of the wheel. In severe cases, risks of wheel "collapsing" or axle breakage may be caused.

Currently, an effective method is an ultrasonic defect inspection method, such as a piezoelectric ultrasonic defect inspection method. A principle thereof is that: if a wheel has a defect such as a gas hole, a crack, and layering (there is air in the defect), when being broadcast to an interface of the defect, an ultrasonic wave may be entirely or partially reflected, the reflected ultrasonic wave is received by a probe, and a depth, a position, and a shape of the defect of a workpiece may be determined according to change features of a waveform.

However, when the ultrasonic defect detection is used, it is required to ensure that an air gap between an ultrasonic probe and the detected wheel is filled with fluid, such as water. Therefore, the wheel is usually separated from a locomotive, and then is placed in water, and the ultrasonic probe is placed in the water to perform detection. It is very difficult to have an overall check on the wheel without separating the wheel from the locomotive.

Therefore, it is necessary to provide an improved system and method to solve the foregoing technical problem.

SUMMARY

In view of the technical problem mentioned above, an aspect of the present application provides a inspection device for detecting a defect of a metal object, where the inspection device includes a main base, at least one main magnetic module, and a main inspection module. The at least one main magnetic module is installed on the main base, for attaching the main base onto the metal object under an action of a magnetic force. The main inspection module is installed on the main base, to detect at least one type of defect of the metal object.

In the inspection device described above, the inspection device includes at least one rolling module, the at least one rolling module is installed on the main base, and when there is a relative motion between the main base and the metal object, the at least one rolling module is configured to reduce a frictional force between the main base and the metal object.

In the inspection device described above, the inspection device includes a lateral base, and the main base and the lateral base are connected together, to form a substantially L-shaped base.

In the inspection device described above, the inspection device includes at least one rotatable member, the at least one rotatable member is installed on the lateral base, and each rotatable member contacts a surface of the metal object, and rotates along the surface, to enable the lateral base to move relative to the surface.

In the inspection device described above, the inspection device includes at least one lateral magnetic module, and the at least one lateral magnetic module is installed on the lateral base, for attaching the lateral base onto the metal object under an action of a magnetic force.

In the inspection device described above, each main magnetic module or each lateral magnetic module includes at least one magnetic element, at least one first fastening element, and at least one second fastening element. The at least one magnetic element is fixed on the at least one first fastening element. Each main magnetic module or each lateral magnetic module is fixed in a corresponding aperture on the main base by using the at least one first fastening element and the at least one second fastening element.

In the inspection device described above, the at least one first fastening element and the at least one second fastening element are regulated to adjust a length that the main magnetic module or the lateral magnetic module protrudes the corresponding aperture, so as to support metal objects of different outer profiles.

In the inspection device described above, the lateral base includes a lateral inspection module installed on the lateral base, and the lateral inspection module is configured to detect at least one type of defect of the metal object.

In the inspection device described above, the main inspection module includes a main ultrasonic probe, the lateral inspection module includes a lateral ultrasonic probe, the main base includes a main fluid groove, and the lateral base includes a lateral fluid groove, where the main fluid groove is injected with fluid, to make a gap between a first surface of the metal object and the main ultrasonic probe filled with fluid. The lateral fluid groove is injected with fluid, to make a gap between a second surface of the metal object and the lateral ultrasonic probe filled with fluid.

In the inspection device described above, the inspection device includes a handle bar, the handle bar is fixed on the main base and the lateral base, the handle bar includes a channel connected to the main fluid groove and the lateral fluid groove, and the channel is used to provide a path for injecting fluid to the main fluid groove and the lateral fluid groove.

In the inspection device described above, the inspection device includes two rolling modules, the two rolling modules are separately installed on two opposite edges of the main base, each rolling module includes a roller body, a shaft, and two bearings, the roller body is fixed on the shaft, and the two bearings are separately accommodated in two bearing holes to support the shaft.

In the inspection device described above, the inspection device includes an encoder, the encoder is fixed with one of the rolling modules, and when the metal object moves from an initial position to a defect position, a position of the defect on a surface of the metal object is determined according to the number of pulses sent by the encoder and a perimeter of the roller body.

Another aspect of the present application provides a wheel defect inspection method, where the method includes at least the following steps: attaching a main base of a inspection device onto a tread of a wheel by using at least one main magnetic module; attaching a lateral base of the inspection device to a side face of the wheel by using at least one lateral magnetic module; and detecting at least one type of defect of the wheel by using at least one of the main inspection module and the lateral inspection module.

In the defect inspection method described above, the method includes: moving the inspection device from a second position to a first position along the tread of the wheel by rotating at least one rolling module; where a magnetic force between the wheel and the inspection device is large enough to overcome weight force of the inspection device, so as to keep the inspection device in the first position.

In the defect inspection method described above, the method includes: injecting fluid into a gap between the tread and a main ultrasonic probe and into a gap between the side face and a lateral ultrasonic probe through a channel, where a flow rate that the fluid flows into the channel is greater than a flow rate that the fluid flows out of the gap.

In the defect inspection method described above, the method includes: adjusting a distance between the tread of the wheel and the at least one main magnetic module by rotating at least one first fastening element and second fastening element, to enable the inspection device to support wheels of different tread profiles.

Yet another aspect of the present application provides a inspection device, where the inspection device includes a first base, a second base, at least one first magnetic module, a first inspection module, and at least one second magnetic module. The at least one first magnetic module is installed on the first base, for attaching the first base onto a wheel under an action of a first magnetic force. The first inspection module is installed on the first base, to detect at least one type of defect of the wheel. The at least one second magnetic module is installed on the second base, for attaching the second base onto the wheel under an action of a second magnetic force.

In the inspection device described above, the inspection device includes a second inspection module installed on the second base, and the second inspection module is configured to detect at least one type of defect of the wheel.

In the inspection device described above, the inspection device includes at least one rolling module, the at least one rolling module is installed on the first base, and when there is a relative motion between the first base and the wheel, the at least one rolling module is configured to reduce a frictional force between the first base and the wheel.

When the wheel defect inspection device and defect inspection method are compared with a conventional apparatus and method, on the one hand, a magnetic force generated by a magnetic module may be used to attach the inspection device onto a wheel that is to be detected, and a rolling module is used to enable the inspection device to keep in the lowest point of the wheel under an action of weight force as the rolling module makes a rolling motion relative to a tread of the wheel, and to automatically implement defect detection for a whole circumference of the wheel. When an ultrasonic probe is used for the inspection module, a fluid channel limited by a handle bar may provide a path for injecting fluid into a fluid tank, so as to provide a transmitted ultrasonic wave with a necessary fluid medium. The inspection device may detect a wheel defect without separating the wheel from a vehicle body, thereby improving portability and operability of defect detection.

BRIEF DESCRIPTION OF DRAWINGS

Embodiments described herein may be understood in a better way by describing the implementation manners with reference to the accompanying drawings. In the accompanying drawings:

FIG. 8 is a schematic cross-sectional diagram of the inspection device shown in FIG. 2 along an A-A line;

FIG. 9 is a schematic cross-sectional diagram of the inspection device shown in FIG. 2 along a B-B line;

FIG. 10 is a cross-sectional diagram of the rotatable member shown in FIG. 7;

DETAILED DESCRIPTION

The following will describe specific implementation manners. It should be noted that, in the specific description process of these implementation manners, in order to make terse and concise descriptions, it is impossible to describe in the specification all features of an actual implementation manner in detail. It should be understood that, in an actual implementation process of any one implementation manner, as in a process of any one project or design project, in order to achieve the developers' specific goals, and in order to meet system-related or business-related limitations, various specific decisions may usually be made, and the decisions may change from one embodiment to another embodiment. In addition, it can also be understood that, although efforts made in the development process may be complicated and lengthy, for a person of ordinary skill in the art related to the content disclosed in the present application, some changes, such as in design, manufacturing, or production, made based on the technical content disclosed in the disclosure are common technical means, and should be construed that the content of the disclosure is not sufficient.

Unless otherwise defined, the technical terms or scientific terms used in the claims and specification should be the ordinary meaning understood by a person of ordinary skill in the technical field. "First", "second" and similar words used in the patent application specification and claims do not denote any order, quantity, or importance, but are just used to distinguish different components. "A" or "an" and other similar words do not denote quantity limitations, but denote that at least one exists. "Comprises" or "comprising" and other similar words imply that an element or object appearing before the "comprises" or "comprising" covers enumerated elements or objects and equivalents elements thereof appearing after the "comprises" or "comprising", without excluding other elements or objects. "Disposed", "connected", or "connecting" and other similar words are neither limited to physical or mechanical connections, nor limited to direct or indirect connections.

"May", "can", "possible", and other words used indicate a possibility of an event in some environments, and possessing a specific attribute, feature or function; and/or represent, by combining with a qualified verb, one or more capabilities, performance, or possibilities. Correspondingly, the use of "possible" indicates that: a modified term is clearly suitable, matchable, or appropriate for a shown capability, function, or purpose. Further, considering existence of some situations, sometimes, the modified term may not be suitable, matchable, or appropriate. For example, in some cases, a result or performance may come out as expected, while in other cases, the result or performance may not come out. This difference is embodied by the word that expresses "possibility".

Figure 1:
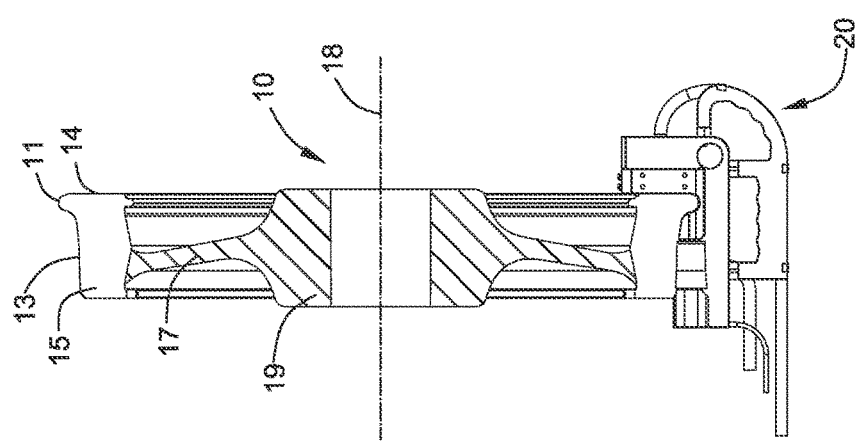
FIG. 1 is a schematic assembly diagram of an inspection device and a wheel.

Referring to FIG. 1, FIG. 1 shows a schematic assembly diagram of a inspection device 20 and a wheel 10. As shown in FIG. 1, in a radial direction from a central spindle (along a position where an axial line 18 is located) of the wheel 10, there are successively, a wheel hub 19, a spoke 17 connected to the wheel hub 19, and a wheel rim 15 connected to the spoke 17. A surface of the wheel rim 15 includes a tread 13, a wheel flange 11, and a side face 14. An interior state of the wheel 10, such as a state of the wheel rim 15, the spoke 17, and the wheel hub 19, or a surface state, such as a state of the tread 13 and the side face 14, is directly related to traffic safety. Therefore, in the implementation manner, the inspection device 20 is configured to detect an interior and/or a surface defect of the wheel 10. The defect may include a shortcoming or fault in any form, such as an interior crack or a surface crack. More specifically, the inspection device 20 may be used to detect a defect of the tread 13, the side face 14, and the wheel rim 15 of the wheel 10, and determine a depth, a position, and a shape of the defect of the wheel 10. The inspection device 20 provided by an embodiment is not limited to detect the defect of the wheel 10, and may further be configured to detect a defect of another metal object.

When the inspection device 20 is used to detect the defect inside the wheel 10 and/or on the surface of the wheel 10, in some implementation manners, the wheel 10 may be separated from a vehicle body, to perform detection separately. In other implementation manners, detection may also be performed without separating the wheel 10 from the vehicle body. For example, heavy equipment is used to elevate the vehicle body, and the inspection device 20 may be automatically attached onto a bottom of the wheel 10 under an action of a magnetic force. More specifically, when the wheel 10 is rotated slowly along the axial line 18 of wheel, in an implementation manner, the inspection device 20 moves relative to the wheel 10 under the combined action of gravity and a magnetic force, so that the inspection device 20 automatically keeps in a bottom of the lowest point of the wheel 10 relative to the wheel 10. In other implementation manners, an additional auxiliary apparatus, such as a support, may be configured to support the inspection device 20, to make the inspection device 20 stable and static in any point where the inspection device 20 closely contacts the wheel 10, such as the highest point of the wheel 10. As the wheel 10 is slowly rotated, both the tread 13 and the side face 14 of the whole wheel have an opportunity to contact the inspection device 20, and the inspection device 20 may detect an interior and/or a surface defect near a position where the inspection device 20 contacts the wheel 10. Therefore, the inspection device 20 may detect a circumference of the whole wheel.

Figure 2:
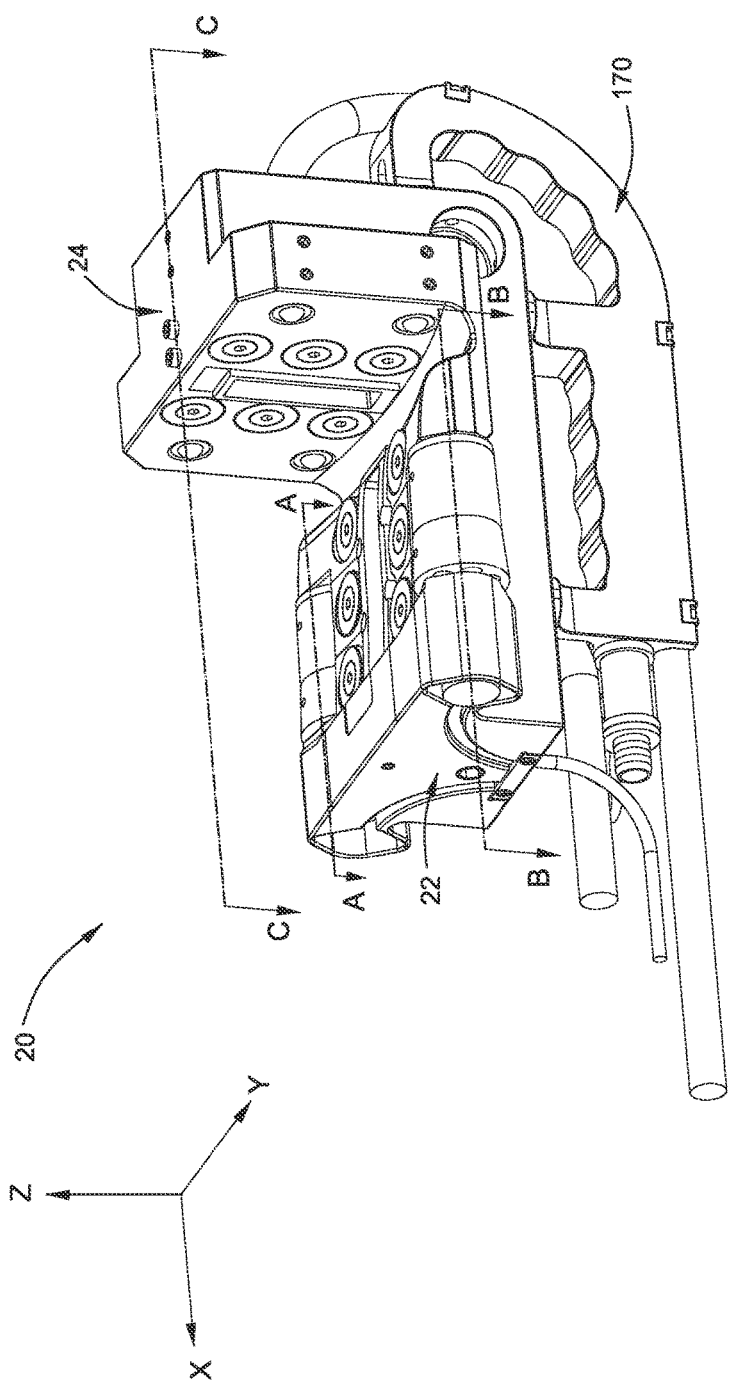
FIG. 2 is a schematic three-dimensional diagram of the inspection device shown in FIG. 1.

Referring to FIG. 2, FIG. 2 is a schematic three-dimensional diagram of the inspection device 20 shown in FIG. 1. The inspection device 20 includes a first detection component 22 along an XY plane. When performing detection for the wheel 10 shown in FIG. 1, the first detection component 22 may be attached onto a surface of the tread 13 of the wheel 10 under an action of a magnetic force, so as to detect a surface defect of the tread 13 and an interior defect of the wheel hub 15.

The inspection device 20 further includes a second detection component 24 along an YZ plane. When performing detection for the wheel 10 shown in FIG. 1, the second detection component 24 may be attached onto a surface of the side face 14 of the wheel 10 under an action of a magnetic force, so as to detect a surface defect of the side face 14 and an interior defect of the wheel hub 15.

To facilitate holding of the first detection component 22 and the second detection component 24, the inspection device 26 further includes a handle bar 170 connected outside the first detection component 22 and the second detection component 24.

In some implementation manners, the inspection device 20 may include the first detection component 22 only or include the second detection component 24 only. With the help of an external support, the first detection component 22 or the second detection component 24 may be successively attached onto the tread 13 and the side face 14 of the wheel 10, so as to perform comprehensive detection for the circumference of the wheel 10. In some implementation manners, the inspection device 20 includes the first detection component 22 and the second detection component 24, the first and second detection components 22 and 24 are discrete components, and the first detection component 22 and the second detection component 24 are connected together, to combine into a substantially L-shaped component with an included angle of approximately 90°. In other implementation manners, the inspection device 20 includes the first detection component 22 and the second detection component 24, and the first and second detection components 22 and 24 are integrally processed as a substantially L-shaped component with an included angle of approximately 90°. The included angle matches an included angle between the tread 13 and the side face 14 of the wheel 10, so that the inspection device 20 and the wheel 10 are clamped.

Figure 3:
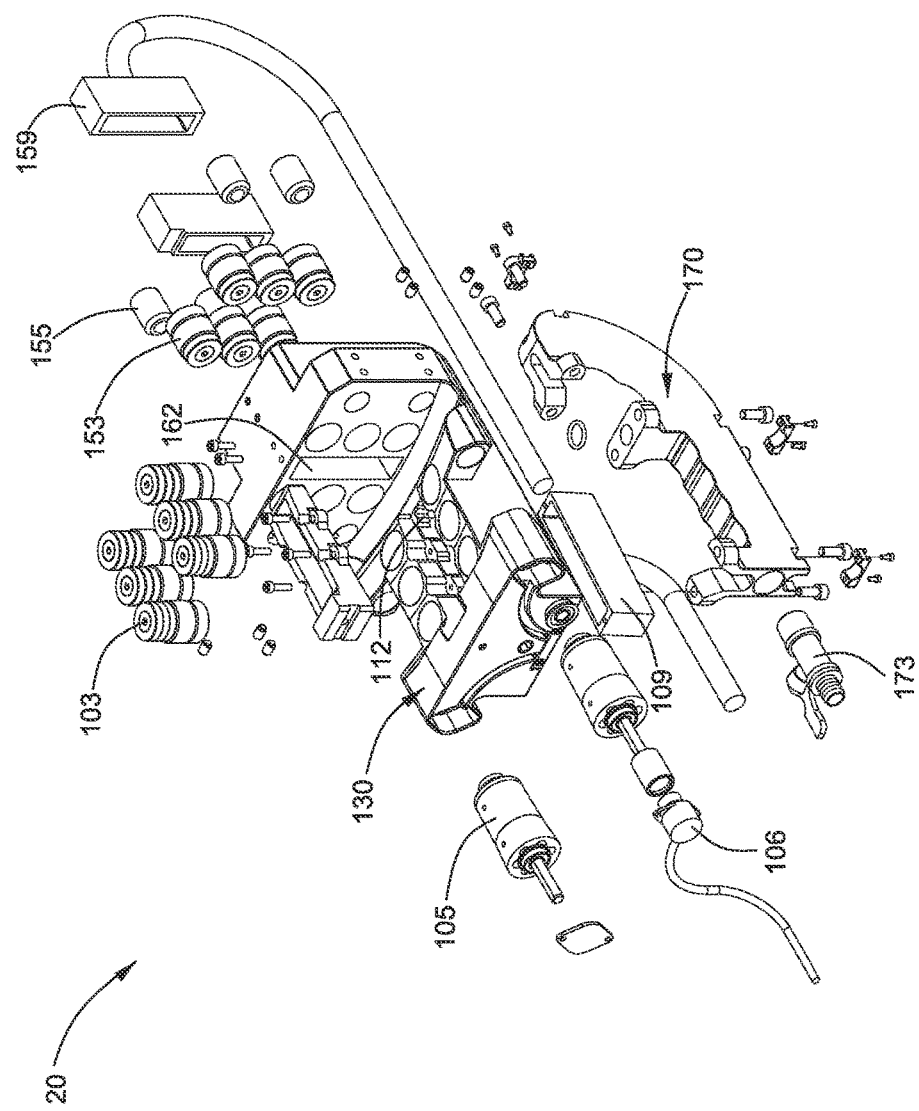
FIG. 3 is a schematic explosive diagram of components of the inspection device shown in FIG. 2.

Referring to FIG. 3, FIG. 3 is a schematic explosive diagram of the inspection device 20 shown in FIG. 2. The inspection device 20 includes a substantially L-shaped base 130, and the substantially L-shaped base 130 includes a plurality of accommodating cavities for accommodating at least one main magnetic module 103, at least one lateral magnetic module 153, a main inspection module 109, a lateral inspection module 159, at least one rolling module 105, and at least one rotatable member 155.

Figure 15:
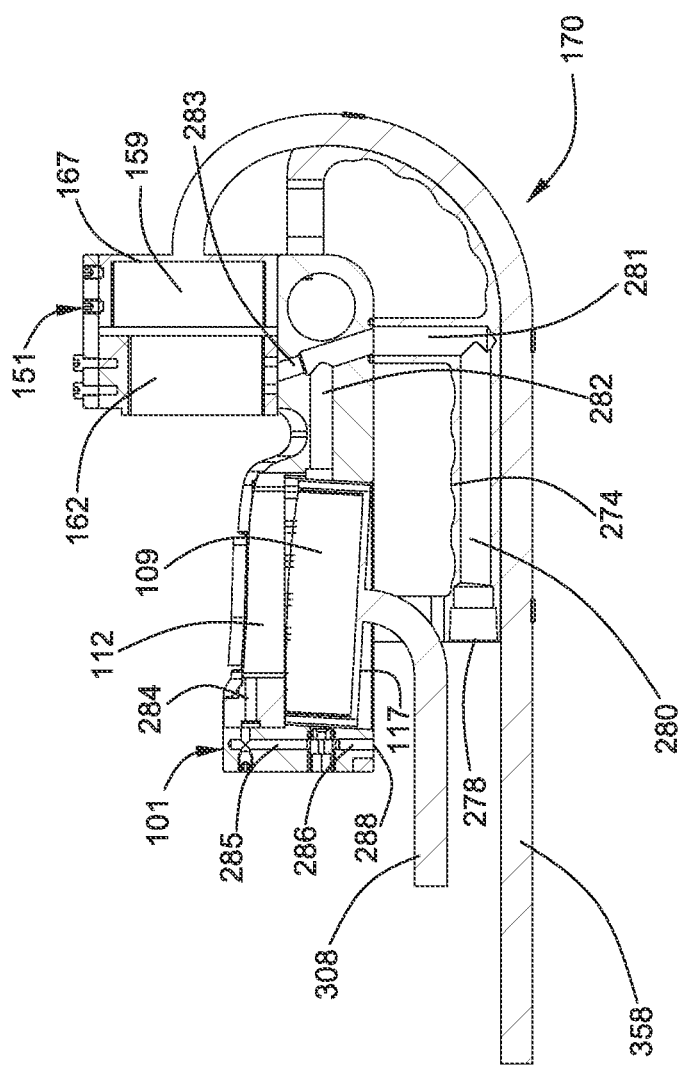
FIG. 15 is a schematic cross-sectional diagram of the inspection device shown in FIG. 2 along a C-C line.

In some implementation manners, the main inspection module 109 and the side inspection module 159 are configured to detect at least one type of defect of at least one of the tread 13, the side face 14, and the wheel rim 15 of the wheel 10 shown in FIG. 1. In an implementation manner, when ultrasonic probe arrays are used for the main inspection module 109 and the lateral inspection module 159, the substantially L-shaped base 130 further includes a main fluid groove 112 and a lateral fluid groove 162. The main fluid groove 112 and the lateral fluid groove 162 are filled with a fluid medium. Ultrasonic waves transmitted by the main inspection module 109 and the lateral inspection module 159 are transmitted to the tread 13 and the side face 14 of the wheel 10 via the fluid medium. In an implementation manner, as shown in FIG. 15, the main inspection module 109 is placed in an accommodating cavity 117 in a lower part of the main fluid groove 112. The lateral inspection module 159 is placed in an accommodating cavity 167 on a right side of the lateral fluid groove 162.

The rolling module 105 closely contacts the tread 13 of the wheel 10 shown in FIG. 1, and the rotatable member 155 closely contacts the side face 14 of the wheel 10. When the wheel 10 is rotated along a direction, such as clockwise, the inspection device 20 is rotated anticlockwise under an action of its own weight force and a magnetic force of the main magnetic module 103 and the lateral magnetic module 153 as rolling friction occurs in a part where the rolling module 105 contacts the tread 13 of the wheel 10, so that the inspection device 20 may automatically keep in the bottom of the lowest point of the wheel 10. When the inspection device 20 is displaced relative to the wheel 10, a part where the rotatable member 155 contacts the side face 14 of the wheel 10 rolls, to reduce a frictional force between the inspection device 20 and the side face 14 of the wheel, sp as to facilitate the inspection device 20 to quickly return to and keep in the bottom of the lowest point of the wheel 10.

After the at least one main magnetic module 103, the at least one lateral magnetic module 153, the main inspection module 109, the lateral inspection module 159, the at least one rolling module 105, and the at least one rotatable member 155 are installed in the accommodating cavities of the substantially L-shaped base 130, to facilitate holding of the substantially L-shaped base 130, the inspection device 20 further includes a handle bar 170 connected outside the substantially L-shaped base 130. When it is required to inject fluid into the main fluid groove 112 and the lateral fluid groove 162 of the substantially L-shaped base 130, the handle bar 170 may be connected to a valve 173. When the valve 173 is opened, fluid may be injected into the main fluid groove 112 and the lateral fluid groove 162 through the valve 173 via a fluid channel limited inside the handle bar 170.

The inspection device 20 further includes an encoder 106, and the encoder 106 is fixed with one of the rolling modules 105. The encoder 106, the main inspection module 109, and the lateral inspection module 159 may communicate with an external processor (not shown), to detect defect and determine a depth, a shape, and a position of the defect of the wheel 10.

The following describes components of the inspection device 20 in detail with reference to FIG. 4 to FIG. 14. FIG. 5 to FIG. 14 are an installation sequence that each component is installed on the base 130, and in other implementation manners, an installation sequence is not limited to the sequence described herein. For example, the installation sequence of the components may be determined according to principles of facilitation and rapidness.

Figure 4:
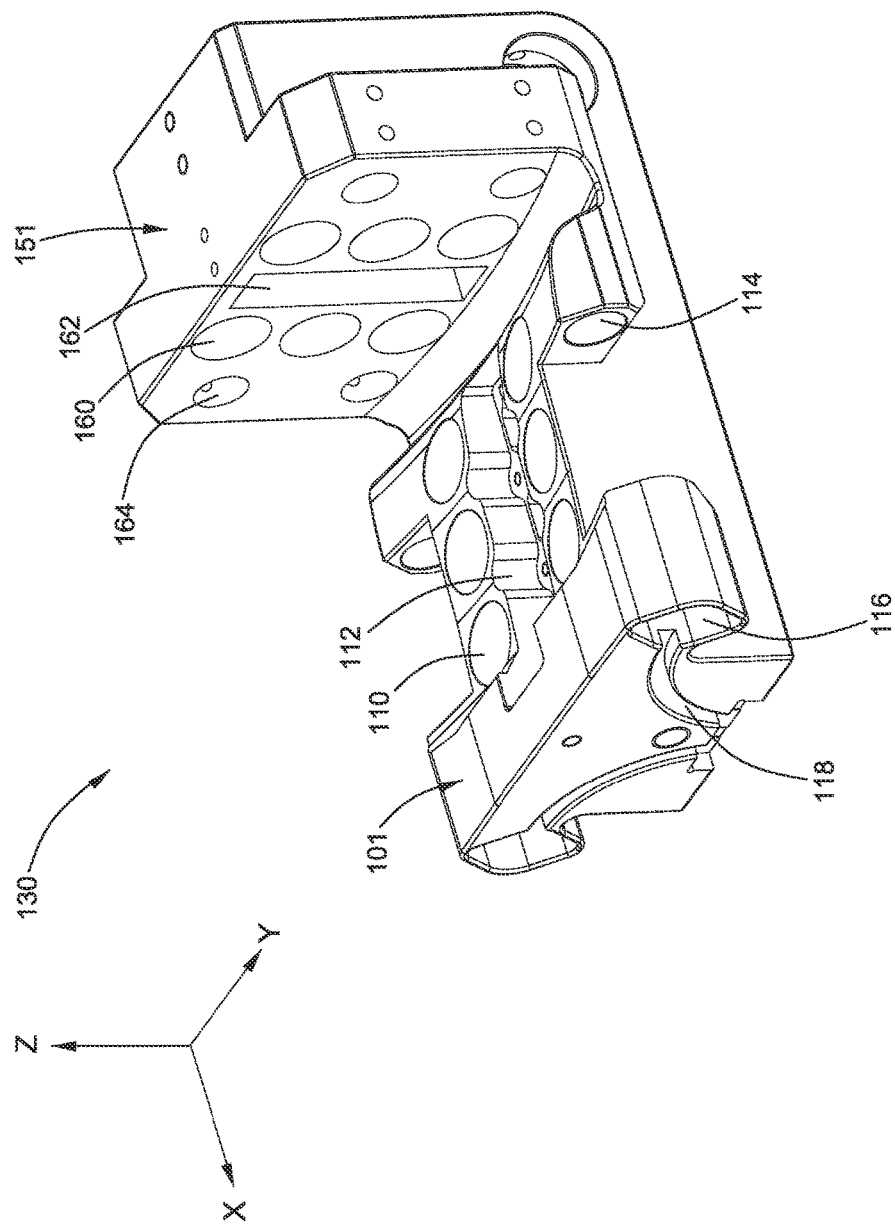
FIG. 4 is a schematic three-dimensional diagram of a base shown in FIG. 2 according to an implementation manner.

Referring to FIG. 4, FIG. 4 is a schematic three-dimensional diagram of the base 130 shown in FIG. 3 according to an implementation manner. In the implementation manner, the base 130 includes a main base 101 and a lateral base 151. The main base 101 includes a plurality of accommodating cavities 110 for accommodating the main magnetic modules 103, an accommodating cavity 117 (see FIG. 15) for accommodating the main inspection module 109, and accommodating cavities 114 and 116 for accommodating the rolling modules 105. When an ultrasonic probe array is used for the main inspection module 109 shown in FIG. 3, the main base 101 further includes a main fluid groove 112, and the main fluid groove 112 is filled with a fluid medium. An ultrasonic wave transmitted by the main inspection module 109 is transmitted to the tread 13 of the wheel 10 via the fluid medium.

In some implementation manners, the plurality of accommodating cavities 110 are through-holes and are symmetrically distributed into two rows. The accommodating cavity 117 and the main fluid groove 112 are disposed in a part between the two rows of accommodating cavities 110. More specifically, as shown in FIG. 15, the accommodating cavity 117 is disposed in a lower part of the part between the two rows of accommodating cavities 110, and the main fluid groove 112 is disposed in an upper part of the part between the two rows of accommodating cavities 110. When the accommodating cavity 117 is used to accommodate an ultrasonic probe array to detect the defect of the wheel 10, the main inspection module 109 transmits an ultrasonic wave along a Z-axis direction, so as to transmit the ultrasonic wave from the tread 13 of the wheel 10 to the wheel rim 15 of the wheel 10 via the main fluid groove 112. In this case, it is necessary to continuously inject fluid such as water to the main fluid groove 112, to use the fluid as a medium required for transmission of the ultrasonic wave. In the implementation manner, the main fluid groove 112 and the accommodating cavity 117 are interconnected. In other implementation manners, a complete through-hole is disposed in the part between the two rows of accommodating cavities 110. When the main inspection module 109 is an ultrasonic probe that needs a fluid medium, a lower part of the through-hole is used to accommodate the ultrasonic probe, and an upper part of the through-hole is used to inject fluid. When the main inspection module 109 is a probe that does not need a fluid medium, such as an electromagnetic ultrasonic probe, the through-hole is used to accommodate the electromagnetic ultrasonic probe 109.

The lateral base 151 includes a plurality of accommodating cavities 160 for accommodating the lateral magnetic modules 153, an accommodating cavity 167 (see FIG. 15) for accommodating the lateral inspection module 159, and an accommodating cavity 164 for accommodating the rotatable member 155. When an ultrasonic probe array is used for the lateral inspection module 159 shown in FIG. 3, the lateral base 151 further includes a lateral fluid groove 162, and the lateral fluid groove 162 is filled with a fluid medium. An ultrasonic wave transmitted by the lateral inspection module 159 is transmitted to the side face 14 of the wheel 10 via the fluid medium.

In some implementation manners, the plurality of accommodating cavities 160 are through-holes and are symmetrically distributed into two rows. The accommodating cavity 167 and the main fluid groove 162 are disposed in a part between the two rows of accommodating cavities 160. More specifically, as shown in FIG. 15, the accommodating cavity 167 is disposed in a right part of the part between the two rows of accommodating cavities 160, and the lateral fluid groove 162 is disposed in a left part of the part between the two rows of accommodating cavities 160. When the accommodating cavity 167 is used to accommodate an ultrasonic probe array to detect the defect of the wheel 10, the lateral inspection module 159 transmits an ultrasonic wave along an X-axis direction, so as to transmit the ultrasonic wave from the side face 14 of the wheel 10 to the wheel rim 15 of the wheel 10 via the lateral fluid groove 162. In this case, it is necessary to continuously inject fluid such as water to the lateral fluid groove 162, to use the fluid as a medium required for transmission of the ultrasonic wave. In the implementation manner, the lateral fluid groove 162 and the accommodating cavity 167 are interconnected. In other implementation manners, a complete through-hole is disposed in the part between the two rows of accommodating cavities 160. When the lateral inspection module 159 is an ultrasonic probe that needs a fluid medium, a right part of the through-hole is used to accommodate the ultrasonic probe, and a left part of the through-hole is used to inject fluid. When the lateral inspection module 159 is a probe that does not need a fluid medium, such as an electromagnetic ultrasonic probe, the through-hole is used to accommodate the electromagnetic ultrasonic probe 159.

In some implementation manners, the lateral base 151 is merely used as a baffle, to have an axial position-limiting function for the wheel 10 shown in FIG. 1. That is, when the wheel 10 shown in FIG. 1 is rotated along the axial line 18, an area limited by the lateral base 151 and the main base 101 matches an outline of the wheel 10, so as to achieve an objective of clamping the wheel 10. In this case, no components are installed on the lateral base 151. That is, no inspection modules for detecting the defect of the wheel 10 are installed on the lateral base 151, and the lateral base 151 does not detect the defect of the wheel 10.

Figure 5:
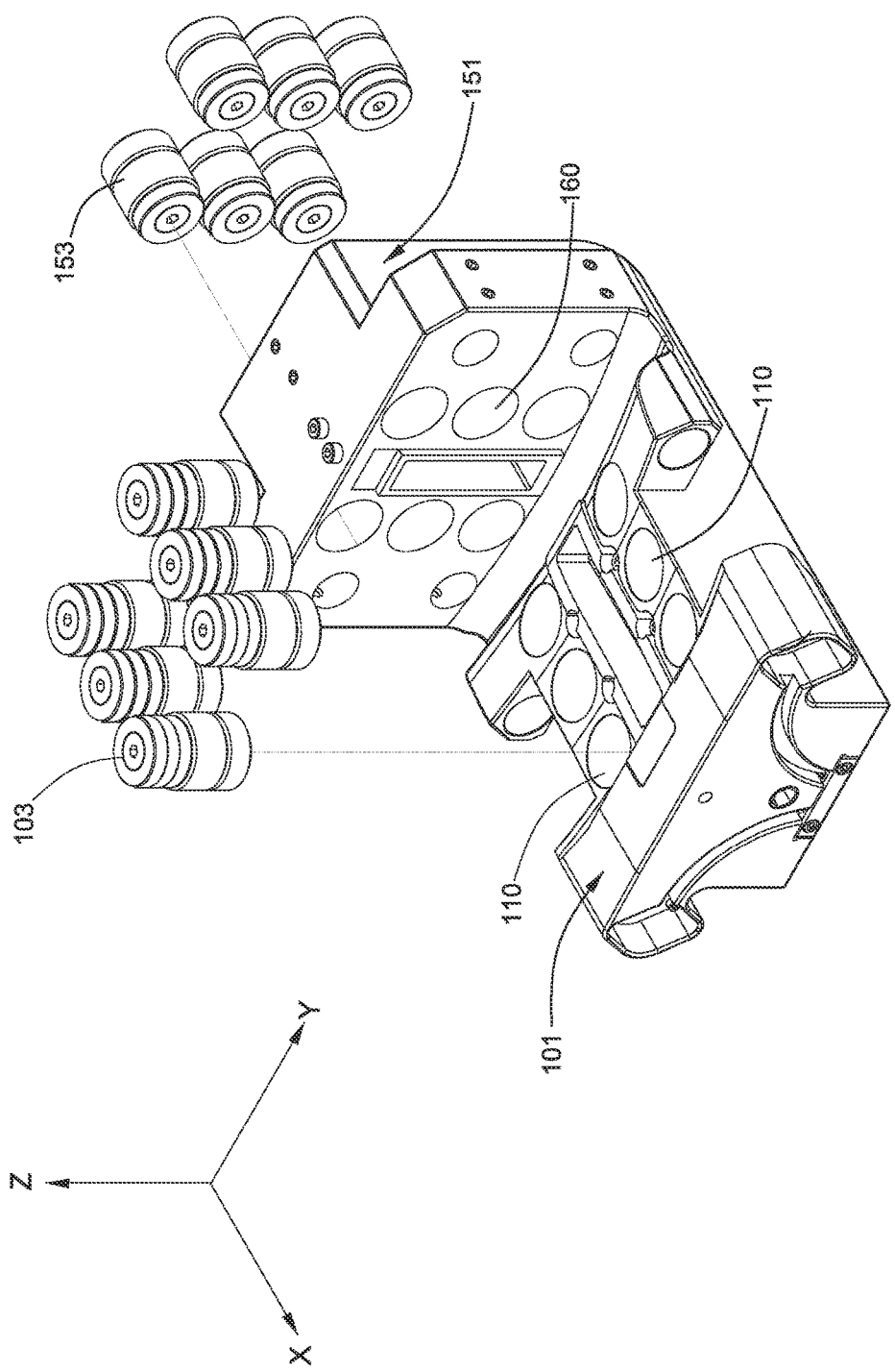
FIG. 5 is a schematic assembly diagram of a main magnetic module, a lateral magnetic module, and a base.

Referring to FIG. 5, FIG. 5 is a schematic assembly diagram of the main magnetic module 103, the lateral magnetic module 153, and the base 130. The accommodating cavities 110 on the main base 101 are arranged as through-holes and are symmetrically distributed into two rows, and the accommodating cavities 160 on the lateral base 151 are arranged as through-holes and are symmetrically distributed into two rows.

A model and a degree of wear of the wheel may affect an outline and a shape of the wheel. In order to ensure that the inspection device 20 may perform detection for wheels of various models and different degrees of wear, each main magnetic module 103 may move up and down in the corresponding accommodating cavity 110 along a Z-axis direction, so as to adjust a distance between each main magnetic module 103 and the tread 13 of the wheel 10 shown in FIG. 1, so that wheels of different treads and outer profiles may be supported. Further, a magnetic force between each main magnetic module 103 and the wheel 10 may be adjusted. Similarly, each lateral magnetic module 153 may move left and right in the corresponding accommodating cavity 160 along an X-axis direction, so as to adjust a distance between each lateral magnetic module 153 and the side face 14 of the wheel 10 shown in FIG. 1, so that wheels of different side faces and outer profiles may be supported. Further, a magnetic force between each lateral magnetic module 153 and the wheel 10 may be adjusted.

Figure 6:
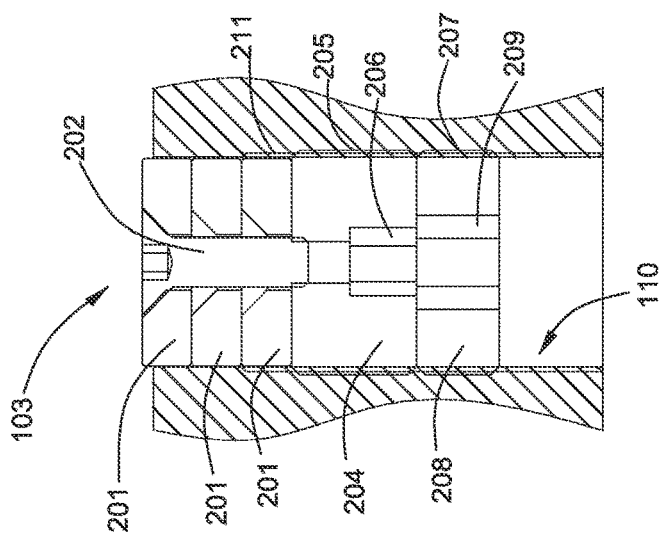
FIG. 6 is a cross-sectional diagram of a main magnetic module.

The main magnetic module 103 and the lateral magnetic module 153 are similar in structure and function. Therefore, with reference to a cross-sectional diagram of the main magnetic module 103 shown in FIG. 6, an example of a relation between the main magnetic module 103 and the main base 101 is described. As shown in FIG. 6, the main magnetic module 103 includes at least one magnetic element 201, at least one first fastening element 204, and at least one second fastening element 208.

The magnetic element 201 may include a magnet or another magnetic force generating element. A magnetic force provided for the inspection device 20 to contact the tread 13 and the side face 14 may be regulated by adjusting a quantity, thickness, and material of the magnetic element 201. In the implementation manner, the magnetic element 201 is fixed on the first fastening element 204 by using a screw 202. An inner wall of the accommodating cavity 110 is arranged with an internal thread 211 partially or entirely. In an implementation manner, the main magnetic module 103 may extend onto the accommodating cavity 110 from a lower part of the accommodating cavity 110 by fitting an external thread 205 of the first fastening element 204 with the internal thread 211 of the accommodating cavity 110. In other implementation manners, the main magnetic module 103 may extend into the accommodating cavity 110 from an upper part of the accommodating cavity 110.

When the threads of the first fastening element 204 and the accommodating cavity 110 are connected and fixed, the second fastening element 208 may be fixed on a bottom of the first fastening element 204 by fitting an external thread 207 of the second fastening element 208 with the internal thread 211 of the accommodating cavity 110. An objective of locking the main magnetic module 103 may be achieved by fitting of first fastening element 204 and the second fastening element 208.

A hexagonal inner cavity 206 may be arranged inside the first fastening element 204, and a hexagonal inner cavity 209 may be arranged inside the second fastening element 208. An external tool may extend into the hexagonal inner cavity 206 or the hexagonal inner cavity 209 to regulate up-down positions of the first fastening element 204 and the second fastening element 208 in the accommodating cavity 110, so as to adjust a length that the main magnetic module 103 protrudes the accommodating cavity 110, thereby supporting wheels of different outer profiles. Similarly, a length that the lateral magnetic module 153 protrudes the accommodating cavity 160 may also be regulated.

Figure 7:
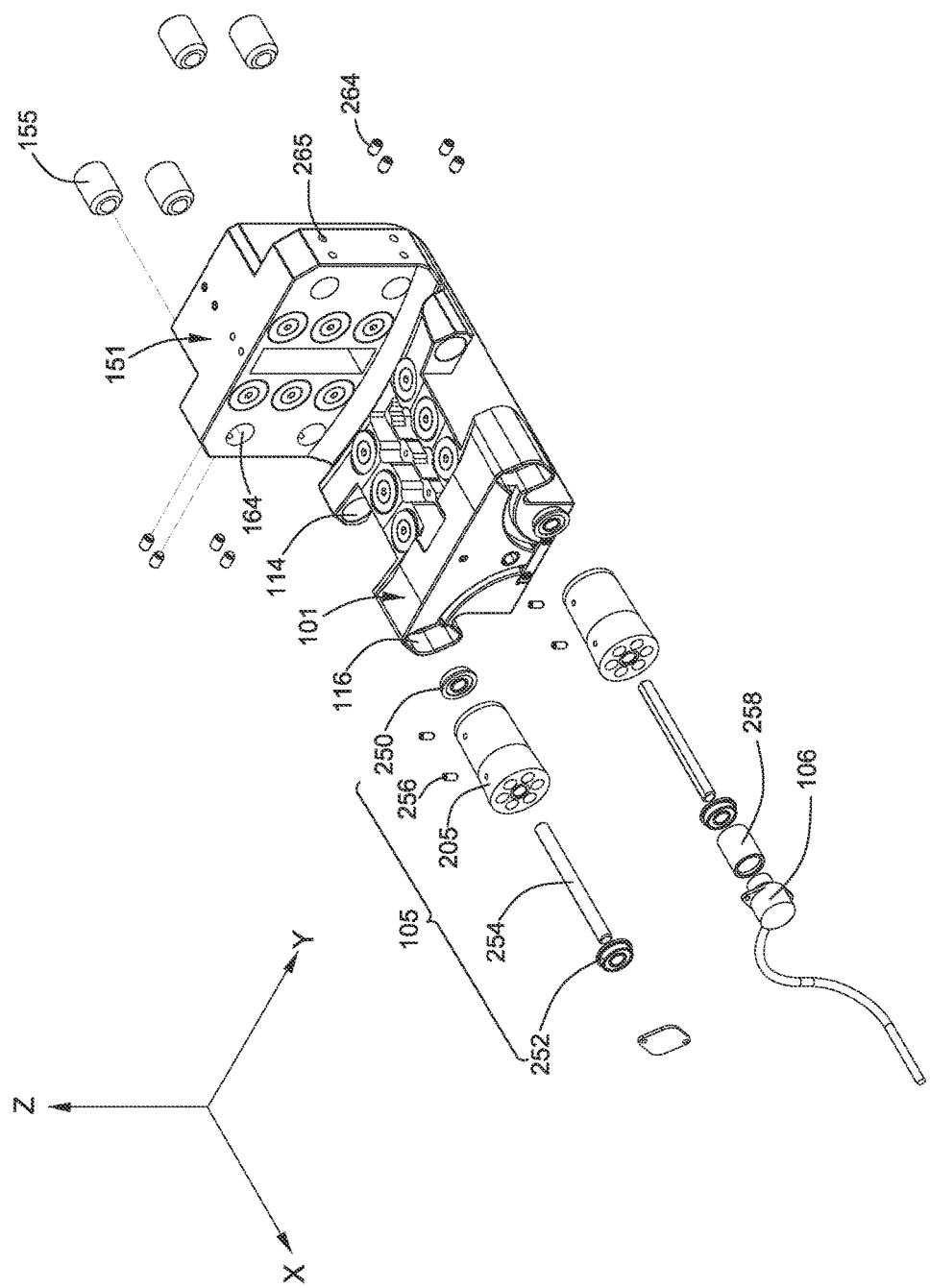
FIG. 7 is a schematic assembly diagram of a rolling module, a rotatable member, and a base.

Referring to FIG. 7, FIG. 7 is a schematic assembly diagram of the rolling module 105, the rotatable member 155, and the base 130. On the one hand, to implement that the inspection device 20 automatically keeps stable in a position of the lowest point of the wheel 10 under an action of gravity, and on the other hand, to reduce rigid friction between the inspection device 20 and the wheel 10, at least one rolling module 105 is arranged on the main base 101, and at least one rotatable member 155 is arranged on the lateral base 151.

More specifically, in the implementation manner, two rolling modules 105 are separately installed on two edges, which are parallel to the X-axis, of the main base 101. As shown in FIG. 7, the rolling module 105 includes a roller body 205, a shaft 254, and two bearings 250 and 252. The roller body 205 is fixed on the shaft 254 by using at least one fixed pin 256, and the two bearings 250 and 252 are separately accommodated in the two accommodating cavities 114 and 116, to support the shaft 254 where the roller body 205 is fixed. The rolling module 105 may be rotated around the shaft 254 in an axial direction, but cannot be moved along the axial direction. In some implementation manners, one accommodating cavity 116 is further used to accommodate the encoder 106.

The rolling module 105 is described in detail with reference to FIG. 8, which is a schematic cross-sectional diagram of a inspection device along the A-A line shown in FIG. 2. After the shaft 254 passes through the roller body 205, a fixed pin 258 shown in FIG. 7 is inserted into a fixing hole 257 arranged on the roller body 205, where the fixing hole 257 is perpendicular to the shaft 254, so that the roller body 205 may be rotated to drive rotation of the shaft 254. The bearings 250 and 252 pass through the shaft 254 and are sleeved on both sides of the roller body 205. The bearing 250 includes a bearing shoulder 251, and when the bearing 250 extends into the accommodating cavity 114, the bearing shoulder 251 may be stuck in an opening of the accommodating cavity 114 and have a position-limiting function in the axial direction. Similarly, the bearing 252 includes a bearing shoulder 253, and when the bearing 252 extends into the accommodating cavity 116, the bearing shoulder 253 may be stuck in one side of an opening of the accommodating cavity 116 and have a position-limiting function in the axial direction. An end cap 118 is fixed on a cavity wall at the other side of the opening of the accommodating cavity 116 by using a retaining screw 120, to play a role of sealing the accommodating cavity 116.

Under an action of a magnetic force, when the wheel 10 is rotated, the wheel 10 may drive the inspection device 20 to move from a first position to a second position. Under an action of gravity, the rolling module 105 and the wheel 10 roll, so that the rolling module 105 moves the inspection device 20 from the second position to the first position along the tread 13 of the wheel 10. In the implementation manner, the first position is the lowest point of the wheel, and the second position is higher than the first position. A magnetic force between the wheel 10 and the inspection device 20 is large enough to overcome weight force of the inspection device 20, to enable the inspection device to keep in the first position or to have small displacement around the first position.

The encoder 106 is described in detail with reference to FIG. 9, which is a schematic cross-sectional diagram of a inspection device along the B-B line shown in FIG. 2. Compared with the rolling module 105 shown in FIG. 8, the accommodating cavity 116 is further used to accommodate a fixing sleeve 258 and the encoder 106. The fixing sleeve 258 is fixed inside the accommodating cavity 116. In the accommodating cavity 116, an end of the fixing sleeve 258 is pressed against the bearing 252, and the other end of the fixing sleeve 258 is used to accommodate the encoder 106. The encoder 106 includes a stator 104 and a rotor 108, where an inner cavity of the rotor 108 is used to sleeve on the shaft 254, and an outer wall of the rotor 108 extends into the fixing sleeve 258. The stator 107 includes a stator shoulder 111. When the encoder 106 extends into the fixing sleeve 258, the stator shoulder 111 may be stuck in the other side of the opening of the accommodating cavity 116, and be fixed on the cavity wall of the accommodating cavity 116 by using the screw 120.

Figure 12:
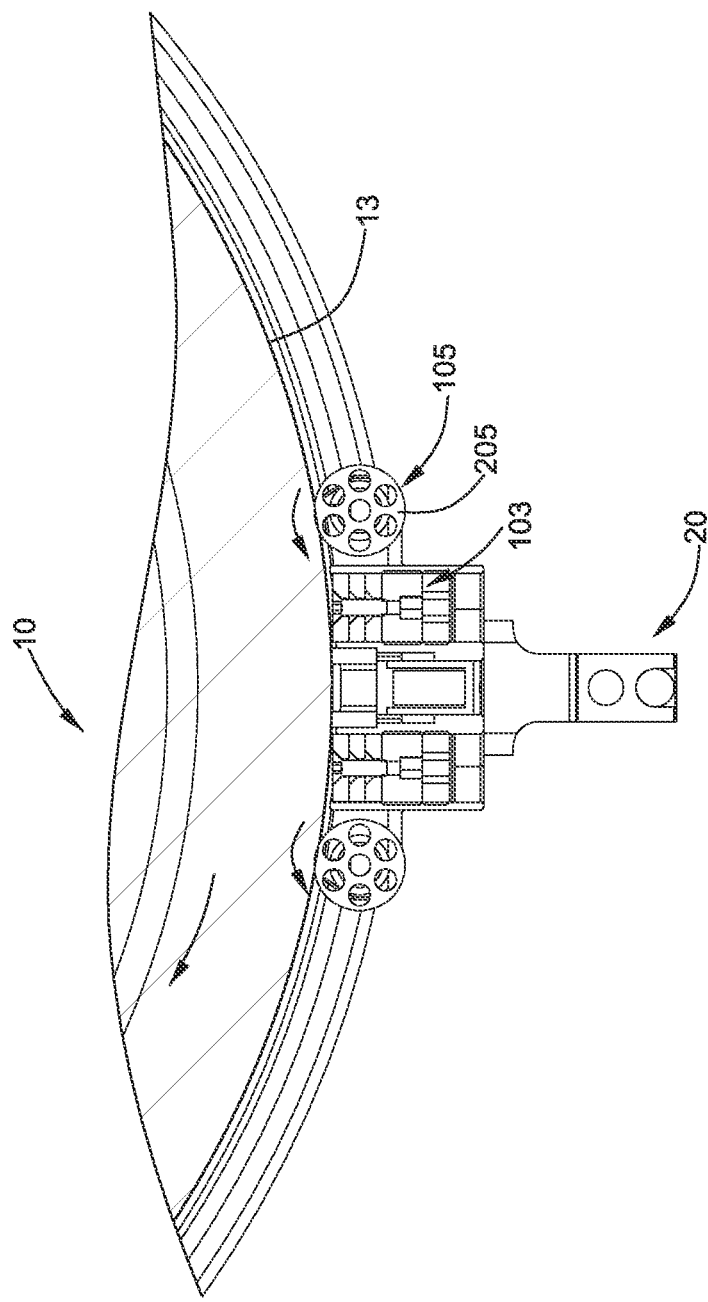
FIG. 12 is a schematic cross-sectional diagram of the inspection device shown in FIG. 1 and a wheel along a rolling module and a main magnetic module.

As shown in FIG. 12, the roller body 205 of the rolling module 105 closely contacts the tread 13 of the wheel 10, and when the wheel 10 is rotated clockwise, the roller body 205 is rotated anticlockwise under an action of a frictional force. Refer to FIG. 9 again. Since the roller body 205 is fixed with the shaft 254, the roller body 205 is rotated to drive rotation of the shaft 254, and further drive rotation of the rotor 108 of the encoder. The encoder 106 may transmit a pulse signal sent by the encoder 106 back to an external processor, so as to determine a position of the defect in the wheel 10.

More specifically, in some implementation manners, a position where the wheel 10 contacts the inspection device 20 in a static state, such as the lowest point of the wheel 10, is an initial position. When the main inspection module 109 and/or the lateral inspection module 159 detect(s) a defect, a position where the inspection device 20 contacts the wheel 10 is a defect position, and a circumference distance $L_{wheel}$ that the wheel 10 is rotated clockwise to the defect position relative to the initial position along the tread 13 may be calculated by the following formula:

$$L_{wheel} = L_{roller} = L * n_{roller} = L * n_{encoder} \quad (1)$$

where when the wheel 10 is rotated clockwise from the initial position to the defect position along the axial line 18, $L_{roller}$ is a circumference distance that the roller body 205 is rotated through, L is a perimeter that the roller body 205 is rotated through a cycle, $n_{roller}$ is a circumference number that the roller body 205 is rotated through, and $n_{encoder}$ is a circumference number that the rotor 108 of the encoder is rotated through. Since a relative motion between the tread 13 of the wheel 10 and the rolling module 105 is rolling, $L_{wheel}$ equals $L_{roller}$; and since the rolling module 105 is rotated to drive rotation of the rotor 108 of the encoder, $n_{roller}$ equals $n_{encoder}$.

It can be known from Formula (1) that, when L is a given value or a numerical value that can be obtained by measurement, it is merely necessary to detect $n_{encoder}$ to obtain $L_{wheel}$, so as to determine the position of the defect on the tread 13 or the side face 14 of the wheel 10 relative to the initial position. $n_{encoder}$ may be calculated by the following formula:

$$n_{encoder} = N_{actual} / N_{2\pi} \quad (2)$$

where $N_{2\pi}$ is the fixed number of pulses, such as 4,096 pulses, sent by the encoder 106 after rotating through a cycle, and $N_{actual}$ is the actual number of pulses detected by the external processor when the defect is detected. When the defect is detected, the circumference distance $L_{wheel}$ that the wheel 10 is rotated through relative to the initial position along the tread 13 may be calculated according to Formulas (1) and (2). Therefore, the external processor may determine the position of defect on the tread 13 or the side face 14 of the wheel 10.

The rotatable member 155 is described in detail with reference to FIG. 10, which is a cross-sectional diagram that the rotatable member 155 is installed on the lateral base 151. In the implementation manner, the rotatable member 155 is a universal rotatable member, and four rotatable members 155 are uniformly distributed and installed on the lateral base 151. More specifically, the rotatable member 155 includes a sphere 289, a plurality of balls 285, and a sphere support 287. The sphere support 287 includes a hollow hemispherical cavity 286, a ball layer composed of the plurality of balls 285 is fully arranged on a surface of the hollow hemispherical cavity 286, and the spheres 289 are placed inside the ball layer. When the sphere 289 contacts the side face 14 of the wheel 10 and has relative displacement, the sphere 289 may be rotated universally. As a result, the inspection device 20 may make a pure rolling motion relative to the wheel 10, so as to reduce a frictional force generated when the inspection device 20 moves relative to the wheel 10. The rotatable member 155 may be inserted into a locating hole 265, which is perpendicular to the accommodating cavity 164, by using a locating pin 264 shown in FIG. 7, to be fixed in the accommodating cavity 164 of the lateral base 151.

In some implementation manners, when the lateral base 151 is used as a baffle to have a position-limiting function in the axial direction for the wheel 10 shown in FIG. 1 and is not used to detect a defect, the lateral base 151 may be uniformly disposed with a plurality of accommodating cavities 164 for accommodating the rotatable members 155. When the wheel 10 is rotated, and when the inspection device 20 moves relative to the wheel 10 under an action of gravity, the rotatable member 155 may make a rolling motion to reduce a frictional force between the lateral base 151 and the side face 14 of the wheel 10.

Figure 11:
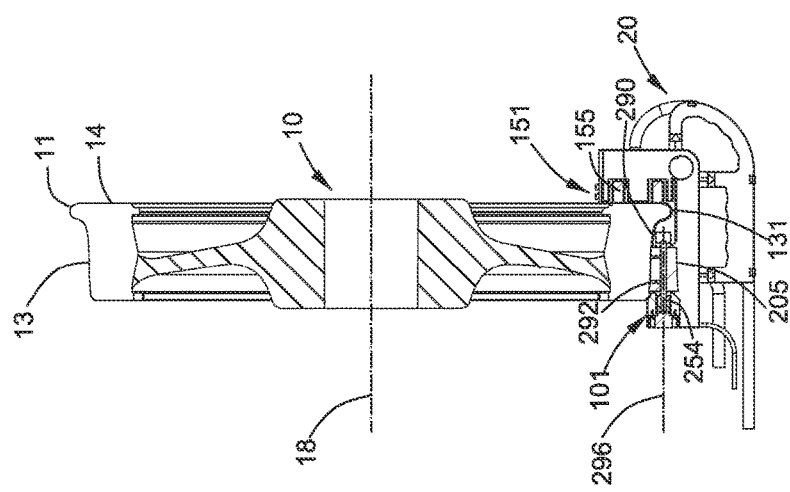
FIG. 11 is a schematic cross-sectional diagram of the inspection device shown in FIG. 1 and a wheel along a rolling module and a rotatable member.

Referring to FIG. 11, FIG. 11 is a schematic cross-sectional diagram of the inspection device 20 shown in FIG. 1 and the wheel along a rolling module and a rotatable member. As shown in FIG. 11, when the inspection device 20 is assembled with the wheel 10, an axial line 296 of the shaft 254 is in parallel with an axial line 18 of the wheel 10, and an outline 292 (which is shown more clearly in FIG. 8 and FIG. 9) of the roller body 205 matches an outline 290 of the tread of the wheel. When the roller body 205 is being processed, the roller body 205 with a different outline 292 may be produced according to the outline 290 of a tread of a wheel of a different model. As shown in FIG. 12, when the two rolling modules 105 are symmetrically installed on both sides of the main base 101, the rolling module 105 may have a radial direction orientation function for the wheel 10. Meanwhile, a distance between the main magnetic module 103 and the tread of the wheel may be adjusted to enable the main magnetic module 103 to fit a space of the wheel 10. As a result, a magnetic force is large enough to ensure that the inspection device 20 is attached onto the wheel 10, and at the same time, a frictional force between the inspection device 20 and the wheel 10 during a relative motion may be reduced.

Refer to FIG. 11 again. When the inspection device 20 is assembled with the wheel 10, the rotatable member 155 closely contacts the side face 14 of the wheel 11, so as to provide an axial direction orientation function for the wheel 10. Meanwhile, a corner where the main base 101 is connected to the lateral base 151 is processed as a groove 131 matching the wheel flange 11 of the wheel 10. When the inspection device 20 is assembled with the wheel 10, the groove 131 may be used to accommodate the wheel flange 11 of the wheel 10, to further provide an orientation function for the wheel 10.

Figure 13:
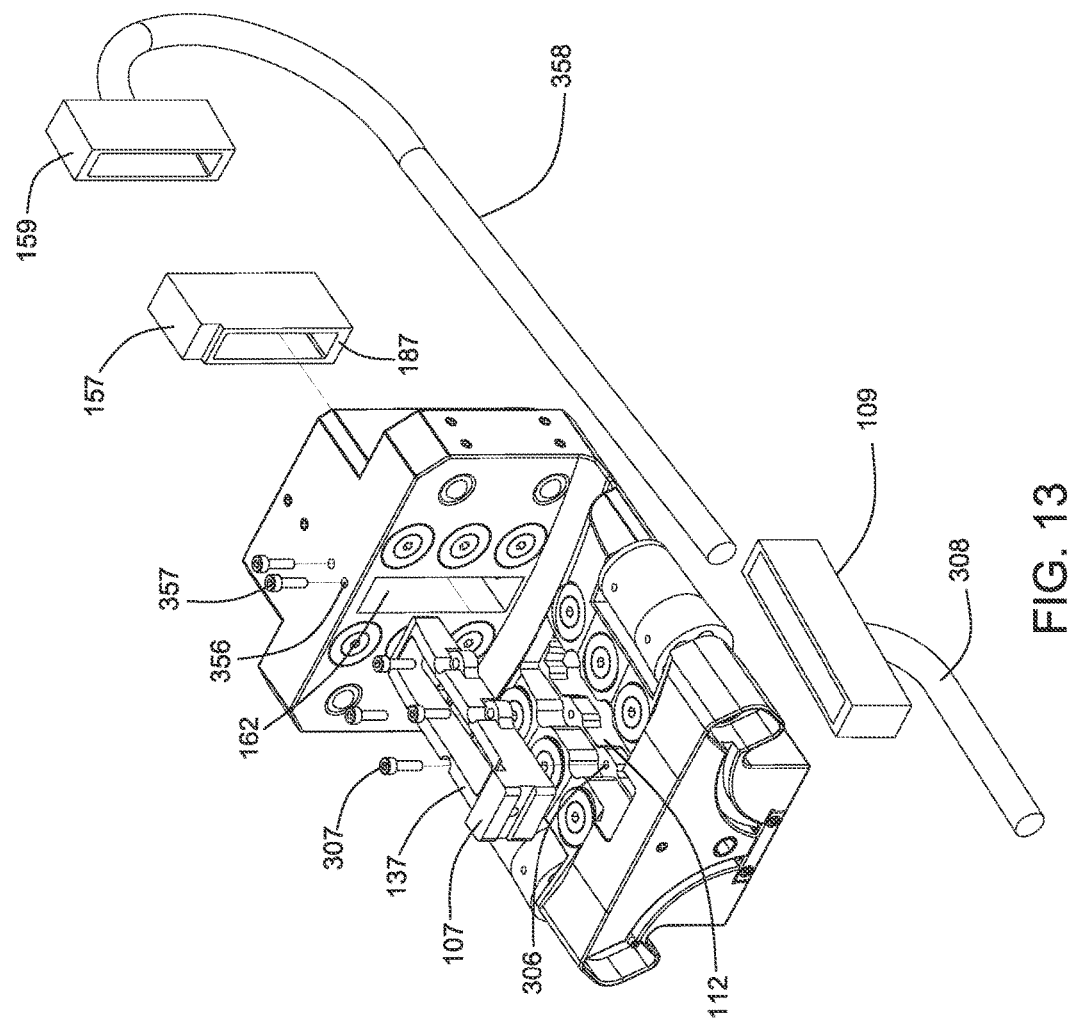
FIG. 13 is a schematic assembly diagram of a main inspection module, a lateral inspection module, and a base.

Referring to FIG. 13, FIG. 13 is a schematic assembly diagram of a main inspection module, a lateral inspection module, and a base. In the implementation manner, ultrasonic probe arrays are adopted for both the main inspection module 109 and the lateral inspection module 159. Therefore, it is required to fill a gap between the main inspection module 109 and the wheel 10 and a gap between the lateral inspection module 159 and the wheel 10 with a fluid medium. The main inspection module 109 is installed in the accommodating cavity 117 shown in FIG. 15. The lateral inspection module 159 is installed in the accommodating cavity 167 shown in FIG. 15. In some implementation manners, a main sealing ring 107 is adhered to a side surface of the main fluid groove 112, and a side sealing ring 157 is adhered to a side surface of the lateral fluid groove 162. As shown in FIG. 13, a plurality of fixing screws 307 are used to fit threaded holes 306 on an edge of the main fluid groove 112, so as to fix the main sealing ring 107. A plurality of fixing screws 357 are used to fit fixing holes 356, so as to fix the side sealing ring 157. When the inspection device 20 is attached onto the wheel 10, an upper surface 137 of the main sealing ring 107 closely contacts the tread 13 of the wheel 10, to have a function of sealing fluid inside the main fluid groove 112, thereby reducing overflowing of the fluid medium in the main fluid groove 112. A left side surface 187 of the side sealing ring 157 closely contacts the side face 14 of the wheel 10, to have a function of sealing fluid inside the lateral fluid groove 162, thereby reducing overflowing of the fluid medium in the lateral fluid groove 162.

A probe signal line of the main inspection module 109 is integrated into a main circuit pipeline 308, and a probe signal line of the lateral inspection module 159 is integrated into a side circuit pipeline 358. The probe signal lines in the main circuit pipeline 308 and the side circuit pipeline 358 are connected to the external processor, to transmit a detected signal to the external processor to be processed, so as to determine whether the detected wheel has a defect and a depth and a shape of the existed defect.

More specifically, in some implementation manners, when the main inspection module 109 sends an ultrasonic signal, the ultrasonic signal may be broadcast in the fluid medium of the main fluid groove 112 and be transmitted to the tread 13 the wheel rim 15 of the wheel 10. When being broadcast to an interface of the defect in the tread 13 or the wheel rim 15, the ultrasonic wave may be entirely or partially reflected, the reflected ultrasonic wave is received by the main inspection module 109, the ultrasonic signal that is reflected back may be transmitted to the external processor via a signal line, and the external processor determines a depth and a shape of the defect of the wheel 10 according to change features of a waveform.

Therefore, according to signals transmitted by the encoder 106 shown in FIG. 7, the main inspection module 109 and the lateral inspection module 159 shown in FIG. 13 to the external processor, the external processor may determine a depth, a position, and a shape of the defect of the wheel 10.

Figure 14:
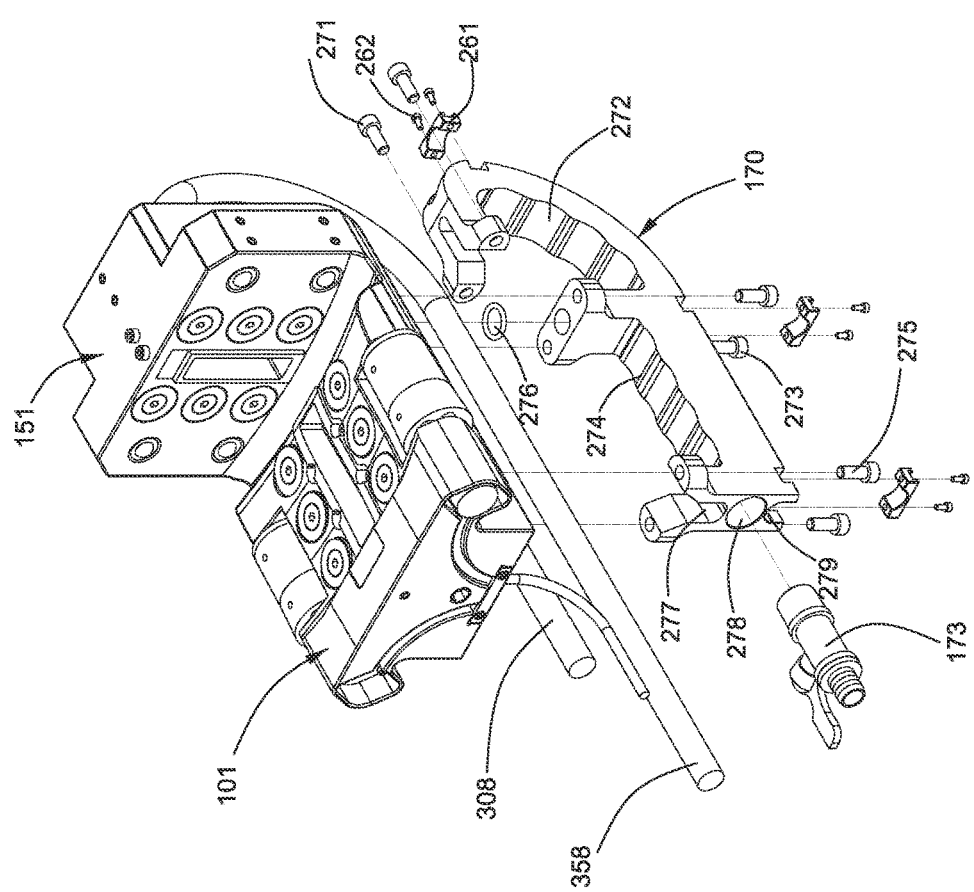
FIG. 14 is a schematic assembly diagram of a handle bar and a base.

Referring to FIG. 14, FIG. 14 is a schematic assembly diagram of the handle bar 170 and the base. Refer to FIG. 8. In order to improve portability of the inspection device 20, the handle bar 170 is disposed with two handle bars 272 and 274 for ease of holding. When a magnetic force between the inspection device 20 and the wheel 10 is large, and it is required to remove the inspection device 20, the handle bars 272 and 274 may be held by hands.

A first end of the handle bar 170 may be permanently connected to the lateral base 151 by using a fixing screw 271. A middle part of the handle bar 170 may be permanently connected to the main base 101 by using a fixing screw 273. A second end of the handle bar 170 may be permanently connected to the main base 101 by using a fixing screw 275. A groove 277 is arranged at the second end of the handle bar 170, and when the handle bar 170 is permanently connected to the main base 101 and the lateral base 151, a space limited by a bottom of the main base 101 and the groove 277 may be used to accommodate and limit a position of the main circuit pipeline 308. A groove 279 extending from the first end to the second end is arranged at a lower part of the handle bar 170. When the handle bar 170 is permanently connected to the main base 101 and the lateral base 151, and after the side circuit pipeline 358 is placed in the groove 279, the first end, the middle end, and the second end of the handle bar 170 are separately fastened with one fastening element 261, and each fastening element 261 is fixed to a corresponding position by using two fixing screws 262, so as to limit a position of the side circuit pipeline 358.

A channel for injecting fluid is further arranged inside the handle bar 170, and the valve 173 is fixed at an entry 278 of the channel. A schematic diagram of the channel for injecting fluid is shown in FIG. 15. A sealing ring 276 is arranged at a joint between the middle part of the handle bar 170 and the main base 101, to seal the channel where fluid enters the main base 101 from the handle bar 170, so as to prevent fluid leakage.

Referring to FIG. 15, FIG. 15 is a schematic cross-sectional diagram of the inspection device shown in FIG. 2 along a C-C line. The entry 278 of the channel for injecting fluid is connected to the valve 173. The channel for injecting fluid includes a channel 280 from the channel entry 278 to the middle part of the handle bar 170 along the handle bar 274, a channel 281 in the middle part of the handle bar 170, and channels 282 and 283, which are in the main base 101 and separately lead to the main fluid groove 112 and the lateral fluid groove 162. When the valve 173 shown in FIG. 14 is in an open state, fluid may be continuously injected into the main fluid groove 112 and the lateral fluid groove 162 through the foregoing channels 280, 281, 282, and 283.

In order to ensure that a space between contact faces of the inspection device 20 and the wheel 10, particularly, spaces between the main inspection module 109 and the lateral inspection device 159 and the wheel 10, is filled with fluid, in some implementation manners, a flow rate of the injected fluid is greater than a flow rate that the fluid overflows the main fluid groove 112 and the lateral fluid groove 162. In some implementation manners, channels 284, 285, and 286 are arranged on the main base 101, to guide fluid in the main fluid groove 112 to flow out from a lower outlet 288 of the main base 101 along the channels 284, 285, 286. In other implementation manners, the overflowing fluid may flow out of the main fluid groove 112 and the lateral fluid groove 162 along any path.

Figure 16:
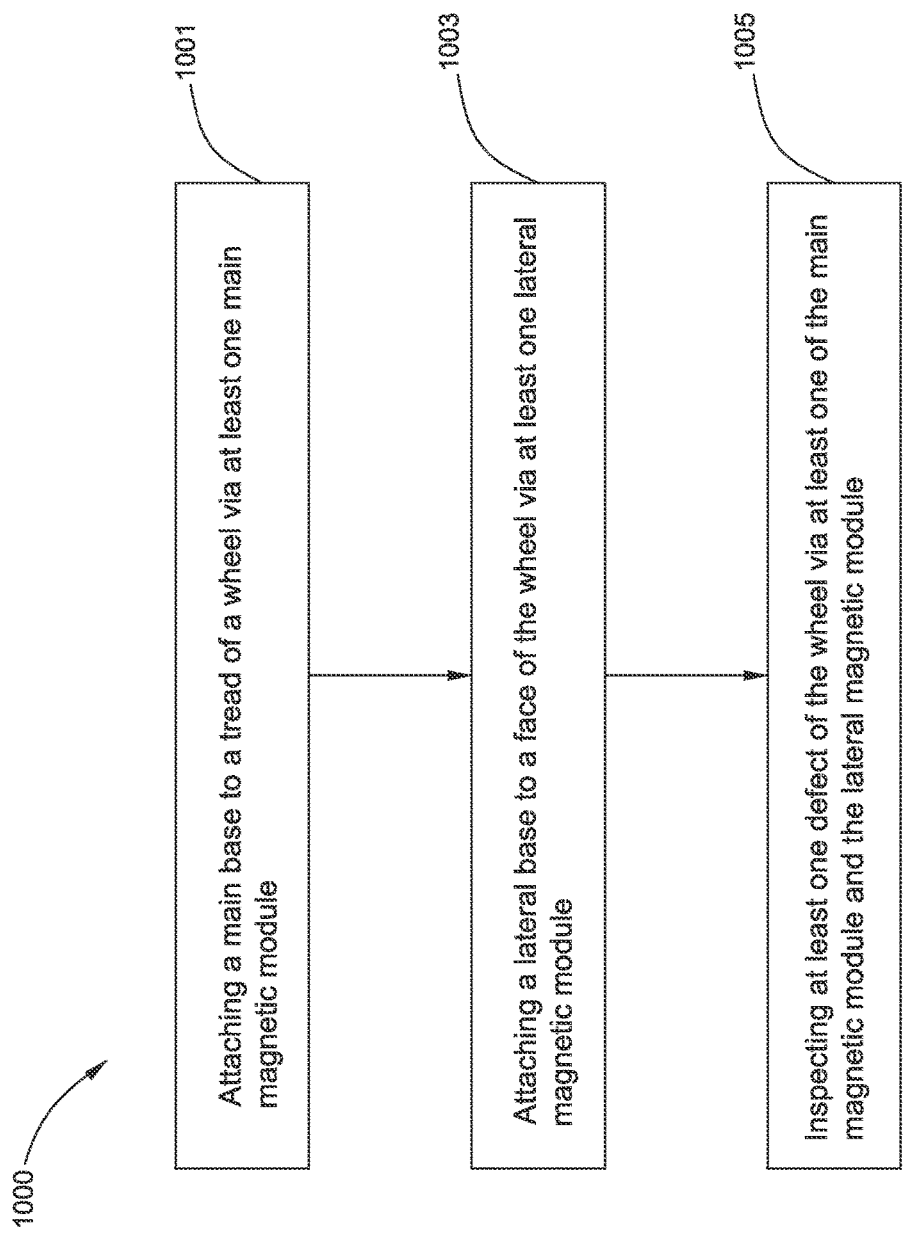
FIG. 16 is a flowchart of a wheel defect inspection method according to an implementation manner.

Referring to FIG. 16, FIG. 16 is a flowchart of a wheel defect inspection method 1000 according to an implementation manner. A sequence of the flowchart shown in FIG. 16 and division of steps in the flowchart are not limited to the shown embodiment. For example, the steps in the flowchart may be executed according to a different sequence. An action in one step may be combined with another one or more steps, or may be divided into a plurality of steps.

In step 1001: attach a main base of an inspection device onto a tread of the wheel by using at least one main magnetic module. In step 1003: attach a lateral base of the inspection device onto a side face of the wheel by using at least one lateral magnetic module. In step 1005: detect at least one type of defect of the wheel by using at least one of the main inspection module and the lateral inspection module.

When the inspection device is configured to detect at least one type of defect of the wheel, the wheel defect inspection method further includes: moving the inspection device from a second position to a first position along the tread of the wheel by rotating at least one rolling module, where the first position is on the bottom of the lowest point of the wheel, and the second position is higher than the lowest point of the wheel. A magnetic force between the wheel and the inspection device is large enough to overcome weight force of the inspection device, so as to keep the inspection device in the first position.

When ultrasonic probes are used as the main inspection module and the lateral inspection device, the wheel defect inspection method further includes: injecting fluid into a gap between the tread and a main ultrasonic probe and into a gap between the side face and a lateral ultrasonic probe through a channel, where a flow rate that the fluid flows into the channel is greater than a flow rate that the fluid flows out of the gap.

When wheels of different models or different degrees of wear are detected, in order to support wheels of different outer profiles, the wheel defect inspection method further includes: adjusting a distance between the tread of the wheel and the at least one main magnetic module by rotating at least one first fastening element and second fastening element, to enable the inspection device to support wheels of different outer profiles.

Although embodiments are described with reference to specific implementation manners, a person skilled in the art should understand that, many modifications and variations may be made. Therefore, it should be aware that, intention of the claims lies in all the modifications and variations covered in a real concept and scope.

What is claimed is:

1. An inspection device for inspecting a metal object, the inspection device comprising:
   a main base;
   a lateral base, the lateral base connected to the main base to form a substantially L-shaped base;
   at least one main magnetic module mounted to the main base for attaching the main base to the metal object under a magnetic force generated between the at least one main magnetic module and the metal object, the at least one main magnetic module including at least one magnetic element, at least one first fastening element, and at least one second fastening element, wherein the at least one main magnetic element is fixed with the at least one first fastening element, and the at least one main magnetic module is fixed with a corresponding aperture using the at least one first fastening element and the at least one second fastening element;
   at least one lateral magnetic module mounted to the lateral base for attaching the lateral base to the metal object under a magnetic force generated between the at least one lateral magnetic module and the metal object, the at least one lateral magnetic module including at least one magnetic element, at least one first fastening element, and at least one second fastening element, wherein the at least one magnetic element is fixed with the at least one first fastening element, and the at least one lateral magnetic module is fixed with a corresponding aperture using the at least one first fastening element and the at least one second fastening element;
   a main inspection module mounted to the main base for detecting at least one defect of the metal object; and
   at least one rolling module mounted on the main base configured to be in contact with a surface of the metal object.

2. The inspection device of claim 1, wherein the at least one rolling module is configured to reduce a friction force between the main base and the metal object when the main base moves relative to the metal object.

3. The inspection device of claim 1, comprising at least one rotatable member mounted to the lateral base, wherein each rotatable member contacts with the surface of the metal object and is rotatable to allow the lateral base to move relative to the surface.

4. The inspection device of claim 1, wherein the at least one first fastening element and the at least one second fastening element are manually operable to adjust a length of the at least one main or at least one lateral magnetic module protruding out of the aperture to support the metal object having different outer profiles.

5. The inspection device of claim 1, wherein the lateral base is further mounted with a lateral inspection module for detecting at least one defect of the metal object.

6. The inspection device of claim 5, wherein the main inspection module comprises a main ultrasound probe and the lateral inspection module comprises a lateral ultrasound probe, wherein the main base comprises a main fluid groove and the lateral base comprises a lateral fluid groove, wherein:
- a fluid is filled in a first gap between a first surface of the metal object and the main ultrasound probe by injecting fluid into the main fluid groove; and
- a fluid is filled in a second gap between a second surface of the metal object and the lateral ultrasound probe by injecting fluid into the lateral fluid groove.

7. The inspection device of claim 6, wherein a handle bar is fixed with the main base and the lateral base, wherein the handle bar comprises channels in fluid communication with the main fluid groove and the lateral fluid groove, the channels are for providing a path to inject fluid into the main fluid groove and the lateral fluid groove continuously.

8. The inspection device of claim 1, comprising two rolling modules which are assembled on two opposite edges of the main base respectively, wherein each rolling module comprises a roller body, a shaft, and two bearings, wherein the roller body is fixed with the shaft and the two bearings are received in two bearing apertures respectively for supporting the shaft.

9. The inspection device of claim comprising an encoder attached to one of the two rolling modules, wherein the encoder is configured to generate a number of pulses that the metal object moves from an initial position to a defect position, to allow the defect position to be determined based at least in part on the number of pulses and a perimeter of the roller body.

10. An inspection method for inspecting a wheel, the inspection method comprising:
- attaching a main base of an inspection device to a wheel tread via at least one main magnetic module;
- attaching a lateral base of the inspection device to a wheel lateral via al least one lateral magnetic module;
- inspecting at least one defect of the wheel via a main inspection module and a lateral inspection module of the inspection device; and
- moving the inspection device from a first position where the inspection device is higher than a lowest point of the wheel to a second position where the inspection device is below the lowest point of the wheel by rotating at least one rolling module along a surface of the wheel tread, wherein the at least one rolling module is in contact with the surface of the wheel.

11. The inspection method of claim 10, comprising:
keeping the inspection device at the second position where a magnetic force generated between the inspection device and the wheel is sufficient to overcome the weight force of the inspection device.

12. The inspection method of claim 10, comprising injecting fluid through a channel into a gap between a main ultrasound probe and a tread surface of the wheel and a gap between a lateral ultrasound probe and a lateral surface of the wheel, wherein a fluid input flow into the channel is larger than an overflow from the gap.

13. The inspection method of claim 10, comprising adjusting a distance between a tread of the wheel and at least one main magnetic module by twisting at least a first and at least a second fastening element to allow the inspection device to support the wheel having different tread profiles.

14. An inspection device, comprising:
- a first base;
- a second base, the second base including a lateral base connected to the first base to form a substantially L-shaped base;
- at least one first magnetic module mounted to the first base for attaching the first base to a first surface of a wheel under a first magnetic force between the at least one first magnetic module and the wheel, the at least one first magnetic module including at least one magnetic element, at least one first fastening element, and at least one second fastening element, wherein the at least one first magnetic element is fixed with the at least one first fastening element, and the at least one main magnetic module is fixed with a corresponding aperture using the at least one first fastening element and the at least one second fastening element;
- a first inspection module mounted to the first base for detecting defects of the wheel;
- at least one second magnetic module mounted to the second base for attaching the second base to a second surface of the wheel under a second magnetic force between the at least one second magnetic module and the wheel, the at least one second magnetic module including at least one magnetic element, at least one first fastening element, and at least one second fastening element, wherein the at least one magnetic element is fixed with the at least one first fastening element, and the at least one second magnetic module is fixed with a corresponding aperture using the at least one first fastening element and the at least one second fastening element; and
- at least one rolling module mounted on the first base, wherein the at least one rolling module is configured to be in contact with a surface of the wheel.

15. The inspection device of claim 14, comprising a second inspection module mounted to the second base for detecting defects of the wheel.

16. The inspection device of claim 14, wherein the at least one rolling module is configured to reduce a friction force between the first base and the tread of the wheel when die first base moves relative to the tread of the wheel.

* * * * *